United States Patent
Isacson et al.

(10) Patent No.: US 9,249,389 B2
(45) Date of Patent: Feb. 2, 2016

(54) METHODS FOR ISOLATING EARLY NEURONS AND NEUROBLASTS

(71) Applicant: THE MCLEAN HOSPITAL CORPORATION, Belmont, MA (US)

(72) Inventors: Ole Isacson, Belmont, MA (US); Jan Pruszak, Freiburg (DE)

(73) Assignee: THE MCLEAN HOSPITAL CORPORATION, Belmont, MA (US)

( * ) Notice: Subject to any disclaimer, the term of this patent is extended or adjusted under 35 U.S.C. 154(b) by 0 days.

(21) Appl. No.: 14/037,475

(22) Filed: Sep. 26, 2013

(65) Prior Publication Data

US 2014/0087464 A1     Mar. 27, 2014

Related U.S. Application Data

(63) Continuation of application No. 12/995,988, filed as application No. PCT/US2009/047565 on Jun. 16, 2009, now abandoned.

(60) Provisional application No. 61/073,301, filed on Jun. 17, 2008.

(51) Int. Cl.
  *C12N 5/0797* (2010.01)
  *C12N 5/0793* (2010.01)
  *C12N 5/079* (2010.01)
  *C07K 14/50* (2006.01)
  *C07K 14/475* (2006.01)
  *A61K 35/54* (2015.01)
  *A61K 35/12* (2015.01)

(52) U.S. Cl.
  CPC .............. *C12N 5/0619* (2013.01); *A61K 35/54* (2013.01); *A61K 35/12* (2013.01)

(58) Field of Classification Search
  None
  See application file for complete search history.

(56) References Cited

U.S. PATENT DOCUMENTS

| | | | |
|---|---|---|---|
| 4,353,888 | A | 10/1982 | Sefton |
| 4,744,933 | A | 5/1988 | Rha et al. |
| 4,749,620 | A | 6/1988 | Rha et al. |
| 4,814,274 | A | 3/1989 | Shioya et al. |
| 5,084,350 | A | 1/1992 | Chang et al. |
| 5,089,272 | A | 2/1992 | Shioya et al. |
| 2006/0099651 | A1 | 5/2006 | Uchida et al. |

FOREIGN PATENT DOCUMENTS

EP          0301777       2/1989

OTHER PUBLICATIONS

Li et al., Trends in Neurosciences, vol. 31 No. 3:146-153, Feb. 5, 2008.*

Bjorklund et al., Cell replacement therapies for central nervous system disorders, Nat. Neurosci., 3:537-544, 2000.

Chung et al., Genetic selection of soxlGFP-expressing neural precursors removes residual tumorigenic pluripotent stem cells and atatenuates tumor formation after transplantation., J. Neurochem., 97:1467-1480, 2006.

Leksell et al, Stereotaxis and nuclear magnetic resonance, J. Neurol. Neurosurg., Psychiatry, 48:14 18, 1985.

Mendez et al., Cell type analysis of functional fetal dopamine cell suspension transplants in the striatum and substantia nigra of patients with Parkinson's disease, Brain, 128:1498-1510, 2005.

Nakagawa et al., Generation of induced pluripotent stem cells without Myc from mouse and human fibroblasts, Nat. Biotechnol., 26:101-106, 2008.

Panchision et al, Optimized Flow Cytometric Analysis of Central Nervois System Tissue Reveals Novel Functional Relationships Among Cells Expressing CD133, CD15, and CD24, Stem Cells, 25:1560 1570 2007.

Penn et al., The adrenal medullary transplant operation for Parkinson's disease: clinical observations in five patients, Neurosurgery, 22:999-1004, 1988.

Perrier et al., Derivation of midbrain dopamine neurons from human embryonic stem cells, Proc. Natl. Acad, Sci. USA, 101:12543-12548, 2004.

Pruszak et al, CD15, CD24 and CD29 Define a Surface Miomarker Code for Neural Lineage Differentiation of Stem Cells, Stem Cells, 27(12):2928-2940, 2009.

Pruszak et al, Markers and Methods for Cell Sorting of Human Embryonic Stem Cell-derived Neural Cell Populations, Stem Cells, 25:2257-2268, 2007.

Sonntag et al., Enhanced yield of neuroepithelial precursors and midbrain-like dopaminergic neurons from human embryonic stem cells using the bone morphogenic protein antagonist noggin, Stem Cells, 25:411-418 2007.

Takahashi et al., Induction of pluripotent stem cells from adult human fibroblasts by defined factors, Cell, 131:861-872, 2007.

Takahashi et al., Induction of pluripotent stem cells from mouse embryonic and adult fibroblast cultures by defined factors, Cell, 126:663-676, 2006.

Vogt et al., Fluorescence intensity calibration for immunophenotyping by flow cytometry, Methods, 21:289-296, 2000.

Wu et al, the development of quantum dot calibration beads and quantitative multicolor bioassays in flow cytometry and microscopy, Anal. Biochem, 364:180-192, 2007.

Yan et al., Directed differentiation of dopaminergic neuronal subtypes from human embryonic stem cells, Stem Cells, 23:781-790, 2005,.

Zeng et al., Stem Cells, 22:925-940 (2004).

Potter et al., Frontiers in Bioscience, 13:806-821 (2008).

Pruszak et al., Stem Cells, 25:2257-2268 (2007).

* cited by examiner

*Primary Examiner* — Daniel E Kolker
*Assistant Examiner* — Stacey N MacFarlane
(74) *Attorney, Agent, or Firm* — Nixon Peabody LLP; David S. Resnick; Leena H. Karttunen Contarino

(57) ABSTRACT

The inventions disclosed herein are based on the identification of novel cell populations derived from human embryonic stem cells and other pluripotent cells. The inventive cell populations may be used for cell therapies for the treatment of various neurological diseases and as substrates in pharmacological assays.

14 Claims, 16 Drawing Sheets

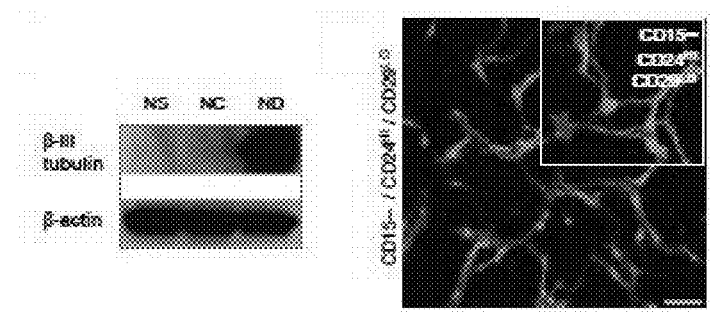
*FIG. 8B*   *FIG. 8C*
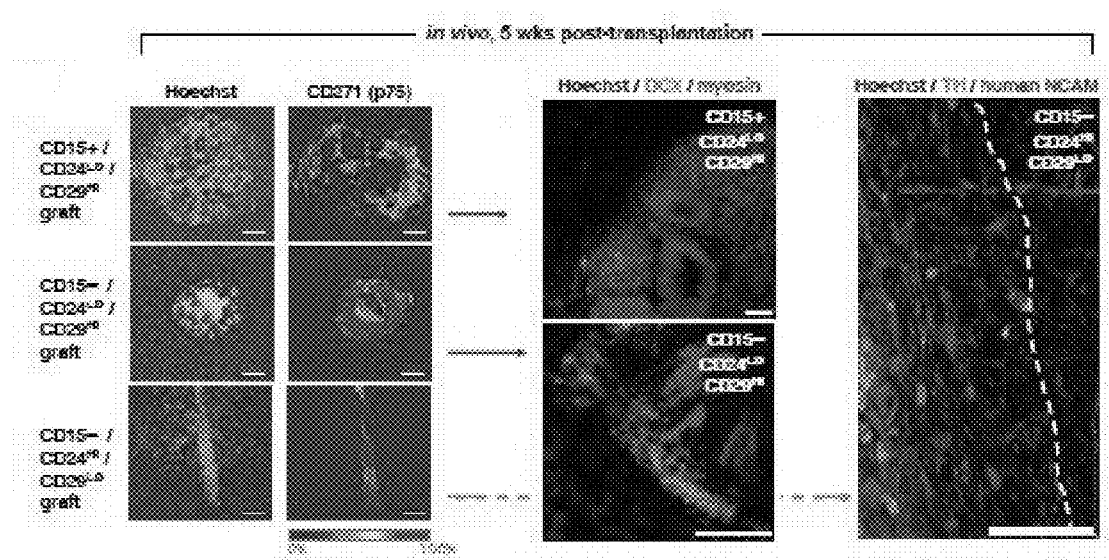
*FIG. 8D*   *FIG. 8E*   *FIG. 8F*
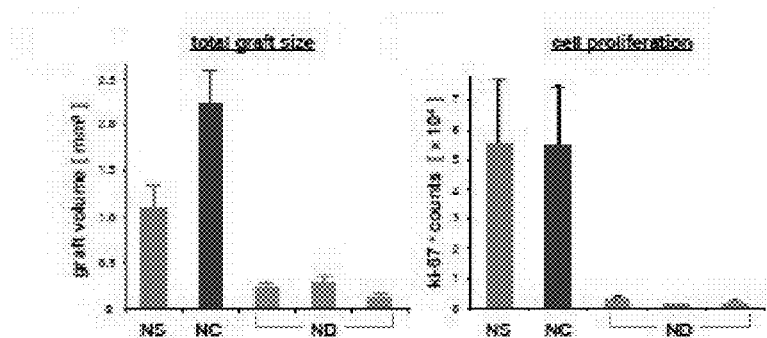
*FIG. 8G*   *FIG. 8H*

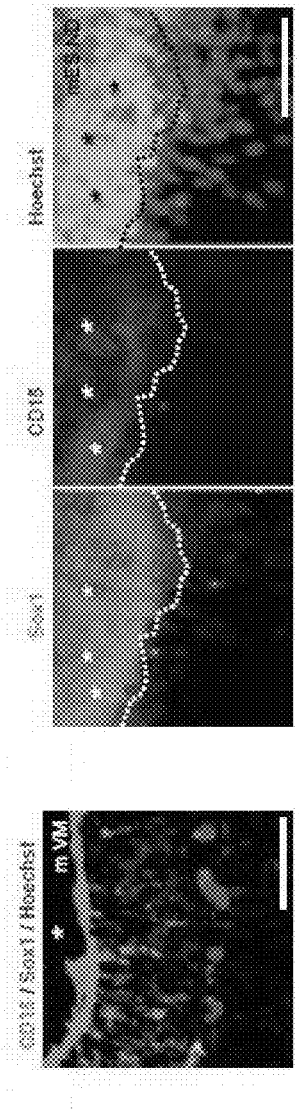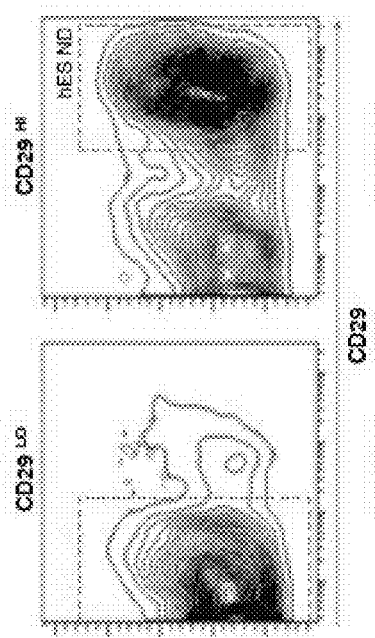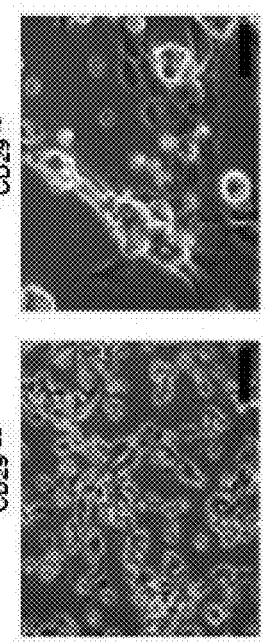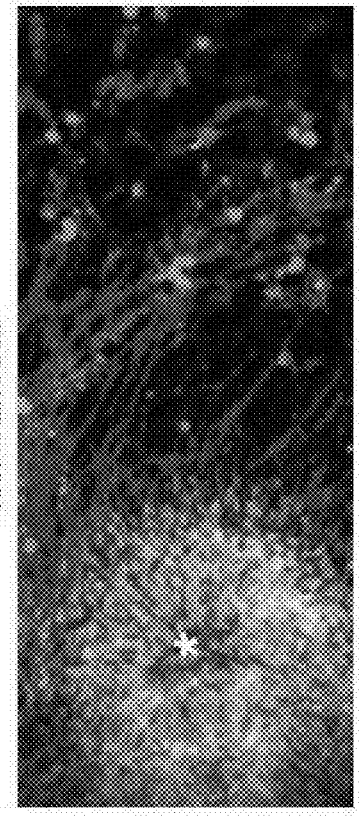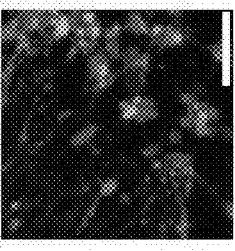
FIG. 9B FIG. 9C FIG. 9D FIG. 9E

METHODS FOR ISOLATING EARLY NEURONS AND NEUROBLASTS

CROSS-REFERENCE TO RELATED APPLICATIONS

This application is a continuation of U.S. patent application Ser. No. 12/995,988 filed Feb. 22, 2011, which is a 35 U.S.C.§371 U.S. National Stage Entry of International Application No. PCT/US2009/047565 filed Jun. 16, 2009, which claims benefit under 35. U.S.C. §119(e) of U.S. Provisional Application No. 61/073,301 filed Jun. 17, 2008, the contents of each of which are hereby incorporated herein by reference in their entireties.

STATEMENT OF GOVERNMENT-SPONSORED RESEARCH

This invention was made with Government support under Grant No. NS039793 awarded by the National Institutes of Health. The Government has certain rights in this invention.

FIELD OF INVENTION

This invention relates to the field of neural cells. Specifically, the invention provides methods and compositions related to purified populations of multipotent neural cells including neural precursor cells, neural crest cells, neuroblasts, and other early neuronal cell populations.

BACKGROUND OF INVENTION

The following discussion of the background of the invention is merely provided to aid the reader in understanding the invention and is not admitted to describe or constitute prior art to the present invention.

A variety of neurodegenerative diseases are characterized by neuronal cell loss. For example, a hallmark of Parkinson's diseases is the progressive loss of midbrain dopaminergic neurons, particularly in the A9 region of the substantia nigra. Other idiopathic and genetic neurodegenerative diseases include, for example, Huntington chorea, characterized by neuronal loss in the frontal lobes, caudate, and basal ganglia, and Alzheimer's disease, affecting the temporal and parietal lobes, the frontal cortex, and the cingulate gyrus.

The regenerative capacity of the adult brain is very limited. Mature neurons are believed to be post mitotic and there does not appear to be significant intrinsic regenerative capacity (i.e., from resident neural stem cells) in response to brain injury and neurodegenerative disease. Further, pharmacological interventions often become increasingly less effective as the susceptible neuronal populations are progressively lost.

Cell transplantation therapies have been used to treat neurodegenerative disease, with moderate success (e.g., Bjorklund et al., Nat. Neurosci. 3: 537-544, 2000). However, widespread application of cell-based therapies will depend upon the availability of large amounts of neuronal precursor cells having consistent characteristics. Preferably, the precursor cell populations will exclusively yield the therapeutic cell type, and cells that give rise to the deleterious effects potentially associated with cell transplantation therapies (e.g., neural tumors) are reduced or eliminated.

Neural cells differentiated in vitro from human embryonic stem cells (hESCs) or other pluripotent cell sources exhibit broad cellular heterogeneity with respect to developmental stage and lineage specification. Current differentiation protocols are able to enrich for particular cell subtypes; however, these protocols are not able to synchronize the birth and development of cell populations (Perrier et al., Proc. Natl. Acad. Sci. USA, 101: 12543-12548, 2004; Sonntag et al., Stem Cells, 25: 411-418, 2007; Yan et al., Stem Cells, 23: 781-790, 2005). Consequently, cells at different stages of maturation are present in the differentiated hESC cultures. Such heterogeneity may impede experimental, clinical, and therapeutic utilization of these cells.

The present invention provides compositions of neural cell populations derived from pluripotent stem cells, and methods for producing the same. The neural cell populations are provided as relatively homogeneous populations at defined stages of maturation and having defined characteristics.

SUMMARY OF THE INVENTION

The present invention is based on the discovery, isolation, and characterization of specific neural cell populations that are derived in vitro from pluripotent cells, including human embryonic stem cells (hESCs), and methods for making and using the same. Specifically identified are populations of early neurons and/or neuroblasts characterized as $CD15^-/CD29^{LO}$ (e.g., $CD15^-/CD24^{HI}/CD29^{LO}$), populations of neural crest cells and/or mesenchymal cells characterized as $CD15^-/CD24^{LO}/CD29^{HI}$, and populations of neural precursor cells characterized as $CD15^+/CD24^{LO}/CD29^{HI}$.

In one aspect, the invention provides a substantially homogenous population of cells, wherein the cells are characterized as $CD24^{HI}$ and express at least one marker selected from the group consisting of TuJ1, MAP2, and doublecortin. In some embodiments, the cells are further characterized as $CD29^{LO}$ and/or $CD15^-$. In other embodiments, the cells further express tyrosine hydroxylase. Preferably, the cells are capable of adopting a neuronal morphology when cultured in the presence of at least one, two, three, or more growth factors including, for example, fibroblast growth factor 8 (FGF8), brain-derived neurotrophic factor (BDNF), basic fibroblast growth factor (bFGF), transforming growth factor type beta-3 (TGF-β3), and glial cell line-derived neurotrophic factor (GDNF). In a preferred embodiment, the cells are characterized as $CD15^-/CD24^{HI}/CD29^{LO}$.

In another aspect, the invention provides a substantially homogenous population of cells, wherein the cells are characterized as $CD24^{LO}$ and $CD29^{HI}$. Optionally, these cells may be further characterized as either $CD15^-$ or $CD15^+$ (i.e., $CD15^-/CD24^{LO}/CD29^{HI}$ or $CD15^+/CD24^{LO}/CD29^{HI}$).

In another aspect, the invention provides therapeutic composition containing one or more of the foregoing cell populations. The therapeutic compositions may contain cells suspended in a physiologically compatible solution or encapsulated in a matrix suitable for in vivo administration.

In another aspect, the invention provides a method for treating a neurodegenerative disease or other brain injury in a patient, by administering to the brain of the patient a therapeutic composition containing one or more of the foregoing cell populations. In some embodiments, the neurodegenerative disease is Parkinson's disease, Alzheimer's disease, Huntington's disease, multiple sclerosis, amyotrophic lateral sclerosis. Brain injuries amenable to treatment according to this aspect of the invention include, for example, traumatic brain injury and ischemic brain injury (e.g., stroke).

In another aspect, the invention provides a method for isolating early neurons and neuroblasts from in vitro culture by (i) culturing pluripotent cells in the presence of one, two, three, or more growth factors that induce at least some of the pluripotent cells to increase expression of TuJ1 relative to pluripotent cells cultured in the absence of the growth factors;

and (ii) selecting cells that express relatively high levels of CD24, wherein the cells are identified as early neurons and neuroblasts. Suitable growth factors include, for example, sonic hedgehog (SHH), fibroblast growth factor-8 (FGF-8), basic fibroblast growth factor (bFGF), and brain-derived neurotrophic factor (BDNF). In some embodiments, the CD15+ cells are removed from the subpopulation. In other embodiments, cells expressing relatively high levels of CD29 (i.e., $CD29^{HI}$ cells) are removed from the subpopulation. Preferably the isolated early neurons and neuroblasts represent not more than 75%, 50%, 35%, 25%, 15%, or 10% of the $CD15^-$ cells from the population cultured in step (i).

In another aspect, the invention provides a method for isolating neural crest cells from in vitro culture by: (i) culturing pluripotent cells in the presence of one, two, three, or more growth factors that induce at least some of the pluripotent cells to increase expression of TuJ1 relative to pluripotent cells cultured in the absence of the growth factor; (ii) removing CD15+ cells from the cells obtained in step (i); and (iii) selecting cells that express relatively high levels of CD29 from the cells obtained in step (i), wherein the cells are identified as neural crest cells. Suitable growth factors include, for example, sonic hedgehog (SHH), fibroblast growth factor-8 (FGF-8), basic fibroblast growth factor (bFGF), and brain-derived neurotrophic factor (BDNF). Preferably the isolated neural crest cells represent not more than 75%, 50%, 35%, 25%, 15%, or 10% of the $CD15^-$ cells from the population cultured in step (i). In other embodiments, the population is enriched for cells that express relatively low levels of CD24.

In another aspect, the invention provides a method for isolating neural precursor cells from in vitro cultures by: (i) culturing a population of pluripotent cells in the presence one, two, three, or more growth factors that induce at least some of the pluripotent cells to increase expression of TuJ1 relative to pluripotent cells cultured in the absence of the growth factors; (ii) removing $CD15^-$ cells from the population cultured in step (i); and (iii) selecting the cells that express relatively high levels of CD29 from the cells obtained in step (i), wherein the cells identified as early neurons and neuroblasts. Suitable growth factors include, for example, sonic hedgehog (SHH), fibroblast growth factor-8 (FGF-8), basic fibroblast growth factor (bFGF), and brain-derived neurotrophic factor (BDNF). Preferably the isolated neural crest cells represent not more than 75%, 50%, 35%, 25%, 15%, or 10% of the $CD15^+$ cells from the population cultured in step (i). In other embodiments, the population is enriched for cells that express relatively low levels of CD24.

In another aspect, the invention provides a method for preparing substantially homogenous populations of cells having a stellate morphology, by: (i) culturing in vitro cells having a stellate morphology; (ii) preparing a fluid composition containing detached cells obtained from the culture of step (i); and (iii) selecting the cells by flow cytometry to generate substantially homogenous cell populations, wherein the flow cytometer fluid pressure is less than about 50 psi (e.g., between about 20 psi and about 50 psi) and the fluid ejection nozzle has a diameter of greater than about 75 μm (e.g., between about 75 μm and about 125 μm). In preferred embodiments, the cells are neurons or neuronal precursor cells.

BRIEF DESCRIPTION OF THE FIGURES

FIG. 8B shows a Western blot of β-III tubulin which was found predominantly in the $CD15^-/CD24^{HI}/CD29^{LO}$) fraction. FIG. 8C is a photomicrograph showing that $CD15^-/CD24^{HI}/CD29^{LO}$ cells cultured after FACS exhibit almost exclusively a neuronal morphology and positivity for neuronal markers such as MAP2 (scale bar=50 µm). FIG. 8D shows a series of photomicrographs of neuronal grafts in adult rat brain (striatum) following transplantation of the indicated cell types. The Hoechst stain (left column of panels) identifies the nucleic of the grafts. The relative absence of p75 in the CD15⁻/CD29$^{LO}$) grafts, relative to grafts of the other cell populations indicates that these grafts contain a large proportion of mature neurons, whereas the other grafts contain a high proportion of undifferentiated cells and/or non-neuronal phenotypes. FIG. 8E shows photomicrographs of neuronal grafts in adult rat brain (striatum) following transplantation of the indicated cell types. The CD15⁺/CD29$^{HI}$ grafts (left panel) contained proliferative neuroepithelial "rosette-like" cells, whereas the CD15⁻/CD29$^{HI}$ grafts (right panel) contained myosin⁺ cell types (scale bar=50 µam). FIG. 8F shows the boundary region between the graft and normal host tissue, demonstrating that the CD15⁻/CD24$^{HI}$/CD29$^{LO}$ cells did not show tumor formation but extended neuronal processes into the host brain tissue. FIG. 8G is a bar graph showing that transplantation of the CD15⁻/CD24$^{HI}$/CD29$^{LO}$ cells did not produce tumors, as indicated by the small graft size. FIG. 8H is a bar graph showing that the number of proliferative ki67-positive cells were greatly reduced in CD15⁻/CD24$^{HI}$/CD29$^{LO}$ cell grafts, compared to grafts of the other cell types.

FIG. 9B is a photomicrograph showing the expression of CD15 in the developing mouse brain (E13). FIG. 9C shows that neuroepithelial cells in culture form typical rosette-like structures (*) and that CD15 expression co-localized with the neural precursor marker Sox2 and the early neuroepithelial marker Pax6. FIG. 9D shows that CD29 was present on neuroepithelial cells co-stained for Pax6 and Sox2 (not shown). The differentiated neuroblasts emerging from these proliferative neuroepithelial clusters were negative/low in CD29 expression. FIG. 9E shows that cultured ES cells that were identified as CD29$^{LO}$) were enriched for cells having a neuronal phenotype, whereas the CD29$^{HI}$ cells mainly contained proliferative clusters and proliferative "flat" cell types.

DETAILED DESCRIPTION OF INVENTION

Figure 1:
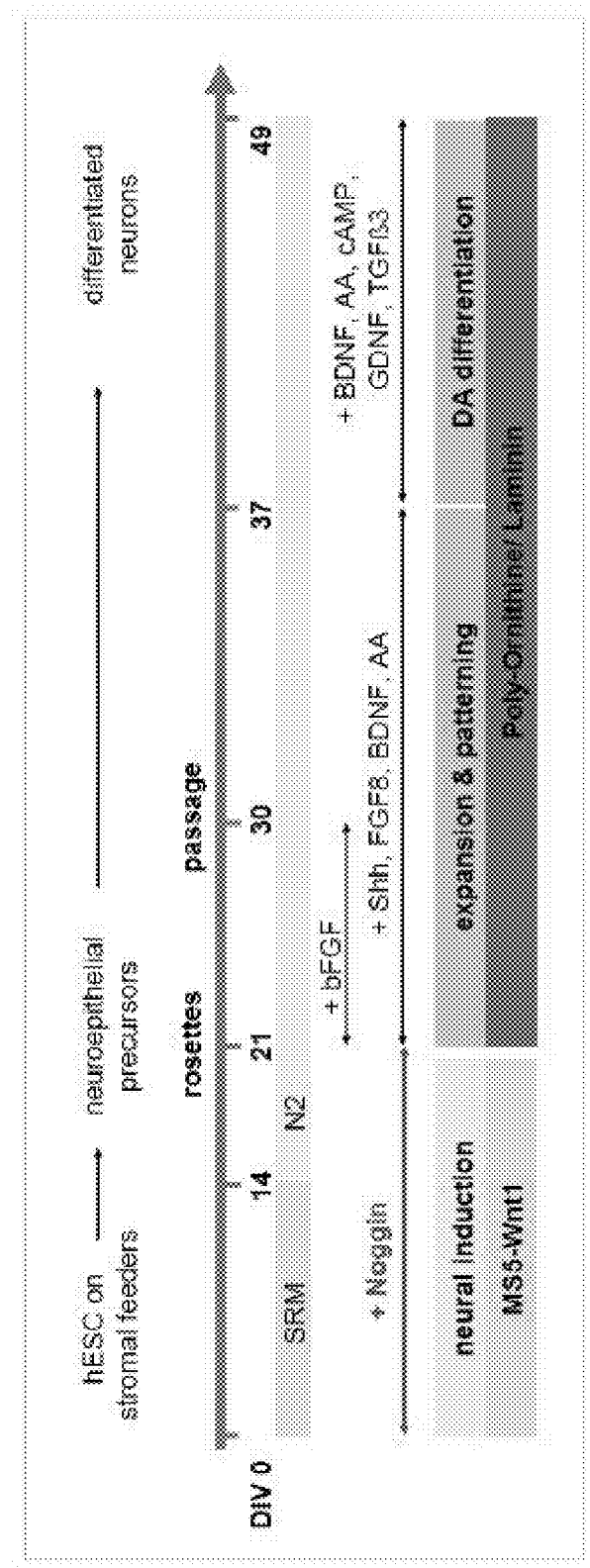
FIG. 1 is a timeline showing an example of certain culture conditions, including growth factors and supplements, used to differentiate hESCs into neural cell populations.

The present invention provides novel populations of multipotent neural cells and methods for producing the same from hESCs or other types of pluripotent cells. The inventive neural cell populations have unique cell surface marker profiles which correspond to defined stages of cellular differentiation and include neural stem/precursor cells, neural crest/mesenchymal cell types, and neuroblasts/early neurons.

The term "embryonic stem cells" (ESC) refers to cells derived from the inner cell mass of blastocysts, blastomeres, or morulae that have been serially passaged as cell lines while maintaining an undifferentiated state (e.g. express TERT, OCT4, and/or TRA antigens). The ES cells may be derived from fertilization of an egg cell with sperm or DNA, nuclear transfer, parthenogenesis, or by means to generate hES cells with hemizygosity or homozygosity in the MHC region.

As used herein, "pluripotent cells" refers to cells capable of differentiating into cell types from any of the three germ lines and also capable of in vitro self-replication, under appropriate conditions, for virtually an indefinite period of time, wherein the daughter cells retain the undifferentiated (pluripotent) characteristics of the parent cells. Pluripotent cells include ESCs but are not necessarily totipotent like ESCs. Other examples of pluripotent cells include induced pluripotent cells (see, for example, Takahashi et al., Cell, 126: 663-676, 2006; Cell, 131: 861-872, 2007; and Nakagawa et al., Nat. Biotechnol. 26: 101-106, 2008), pluripotent cells derived by nuclear transfer, and pluripotent cells isolated from umbilical cord blood or adult blood.

As used herein, "multipotent neural cells" refers to cells which have partially differentiated along a neural cell pathway and express some neural markers. Multipotent neural cells may differentiate into neurons or glial cells and specifically include neural precursor cells, neural crest cells, and neuroblasts. Specific examples of multipotent neural cells described herein include adult- and embryo-derived neural stem cells, and neural cells that are characterized as CD15⁻/CD24$^{HI}$/CD29$^{LO}$, CD15⁻/CD24$^{LO}$/CD29$^{HI}$, and CD15⁺/CD24$^{LO}$/CD29$^{HI}$.

As used herein, "CD15" refers to the cell surface antigen commonly known as cluster of differentiation (CD) 15. CD15 is also known as the Lewis-X antigen, SSEA-1, and 3-fucosyl-N-acetyl-lactosamine.

As used herein, "CD24" refers to the heat-stable small cell lung carcinoma cluster 4 antigen. It is recognized that "CD24$^{LO}$" and "CD24$^{HI}$" may be used as relative or absolute terms when used to compare the level of CD24 between cells within a population or between populations, respectively. For example, when pluripotent cells are cultured in vitro and selected according to the method of this invention, the CD24$^{LO}$ cells represent not more than the 50%, 40%, 30%, 25%, 20%, 15%, 10%, or 5% of cells of the population expressing the lowest level of CD24. Likewise, CD24$^{HI}$ cells represent not more than the 50%, 40%, 30%, 25%, 20%, 15%, 10%, or 5% of cells of the population expressing the highest level of CD24. Thus, when selecting cells of a single population, on the basis of CD24 expression levels, no extrinsic reference is required. Alternatively, when comparing CD24 expression level of the inventive cells to other cell types, CD24$^{HI}$ cells express CD24 at levels comparable to at least about 25%, 50%, 75%, or more of the expression level of mature neurons or the early neurons/neuroblasts of this invention. Preferably, CD24$^{LO}$ cells express CD24 at not more than 1%, 5%, 10%, or 20% of the expression level of mature neurons or the early neurons/neuroblasts of this invention.

As used herein, "CD29" refers to integrin beta-1. It is recognized that "CD29$^{LO}$" and "CD29$^{HI}$" may be used as relative or absolute terms when used to compare the level of CD29 between cells within a population or between populations, respectively. For example, when pluripotent cells are cultured in vitro and selected according to the method of this invention, the CD29$^{LO}$ cells represent not more than the 50%, 40%, 30%, 25%, 20%, 15%, 10%, or 5% of the population expressing the lowest level of CD29. Likewise, CD29$^{HI}$ cells represent not more than the 50%, 40%, 30%, 25%, 20%, 15%, 10%, or 5% of the population expressing the highest level of CD29. Thus, when selecting cells of a single population, on the basis of CD29 expression levels, no extrinsic reference is required. Alternatively, when comparing CD29 expression level of the inventive cells to other cell types, CD29$^{HI}$ cells express CD29 at levels comparable to at least about 25%, 50%, 75%, or more of the expression level of human ES cells (e.g., human ES cell lines H1 and/or H9) or the neural precursor cells of this invention. Preferably, CD29$^{LO}$ cells express CD29 at not more than 1%, 5%, 10%, or 20% of the expression level of human ES cells. Alternatively, CD29$^{LO}$ cells express CD29 at about the same level as mature neurons.

By "a substantially homogenous cell population" is meant a population or sample of cells which contain a majority (i.e., at least 50%) of cells having the trait(s) of interest. In preferred embodiments, substantially homogenous populations contain at least 60%, at least 70%, at least 80%, at least 90%, or more of the cells having the trait(s) of interest.

By "derived in vitro from a pluripotent cell," when referring to a cell or population of cells of the invention, is meant any cell or population of cells which is cultured in vitro from a pluripotent cell in which the culture conditions (e.g., composition of the culture medium, presence of feeder cells, etc.) are specifically derivatized to induce the pluripotent cell to adopt a particular phenotype and/or to express certain intracellular or plasma membrane-bound proteins. Cells that are derived in vitro from a pluripotent cell may remain pluripotent, may be multipotent, or may be terminally differentiated into a mature phenotype.

Flow Cytometry and Fluorescence-Activated Cell Sorting (FACS)

Flow cytometry is a well-known technique for analyzing and sorting cells (or other small particles) suspended in a fluid stream. This technique allows simultaneous analysis of the physical and/or chemical characteristics of single cells flowing through an optical, electronic, or magnetic detection apparatus. As applied to FACS, the flow cytometer consists of a flow cell which carries the cells in a fluid stream in single file through a light source with excites the fluorescently labeled detection marker (for example, antibody) and measures the fluorescent character of the cell. The fluid stream is then ejected through a nozzle and a charging ring, under pressure, which breaks the fluid into droplets. The flow cell device and fluid stream is calibrated such that there is a relatively large distance between individual cells, resulting in a low probability that any droplet contains more than a single cell. The charging ring charges the droplets based on the fluorescence characteristic of the cell which is contained therein. The charged droplets are then deflected by an electrostaticly-charged deflection system which diverts the droplets into various containers based upon their charge (related to the fluorescence intensity of the cell).

Flow cytometry is a particularly useful technique for sorting and characterizing cells having a basic ovoid morphology, with blood cells being the prototypical candidates. Neuronal cells begin to adopt a stellate or dendritic morphology at early stages of differentiation. Detachment of neuronal cells from the solid culture substrate, followed by pruning of the dendritic processes during flow cytometry places a great deal of stress on the cells, making them less reliable in later scientific procedures. As described herein, the basic flow cytometry methodology may be modified to specifically accommodate neuronal cell types in a manner that reduces the stresses placed on the cells, rendering them more amenable for later culture and clinical use.

Two important parameters that may be varied during in the flow cytometry process are the nozzle diameter and the fluid ejection pressure. The stress placed on the neuronal cells may be reduced by increasing nozzle diameter and/or reducing the ejection pressure. These parameters must be optimized for each particular stellate (e.g., neuronal) cell type used in order that the accuracy of the cell sorting method is maintained. For example, an unduly large reduction in fluid/ejection pressure may result in a plurality of cells being trapped in each ejected fluid droplet. This will result in a systematic over-estimation of the labeled cellular marker. If the pressure is sufficiently low, it will also improperly result in a bimodal (or higher order) sorting distribution, wherein the particles tend to sort on the number of cells captured in each particle rather than the signal obtained from each cell (i.e., two cells will have about twice the signal intensity of one cell). Likewise, the nozzle diameter suitable for use with each cell type and at each fluid pressure must also be optimized. Large nozzle diameters are beneficial for large and stellate cells like neurons and neuronal stem cells. However, large nozzle diameters, combined with low fluid pressures result droplets that are unduly large or, in extreme cases, not formed. Large droplets therefore also increase the likelihood of capturing more than one cell in each fluid droplet.

Quantitative flow cytometry is a variation on the basic flow cytometry technique which is useful for inter-experimental and inter-laboratory comparison of cytometric data. (see, for example, Flow Cytometry Principles for Clinical Laboratory Practice: Quality Assurance for Quantitative Immunophenotyping, Owens and Loken, Wiley Life Sciences, 1994, hereby incorporated by reference). Typically, quantitative flow cytometry relies on a set of calibration beads having a fluorophore that matches the emission wavelength of the fluorophore used to characterized the experimental cells. One method for creating calibration beads utilizes streptavidin-labeled fluorescent quantum dots (semiconductor nanoparticles with tunable optical properties) which may be attached to biotinylated calibration beads (e.g., polystyrene beads) (see, for example, Wu et al, Anal. Biochem, 364: 180-192, 2007). The fluorescence of the beads is then correlated with the fluorescence intensity of a solution of known concentration and the intensity of a suspension of beads bearing the same fluorophores. The equivalence of fluorescence radiance of the beads to the solution is known as the molecules of equivalent soluble fluorophores (MESF), where the MESF value is equal to the known number of molecules in solution. Commercially available calibration beads are available, for example, from Invitrogen (Carlsbad, Calif.; LinearFlow® microspheres).

The calibration beads may be used to construct a calibration curve that relates the flow cytometer histogram channel number to the MESF value of the beads (Vogt et al., Methods 21: 289-296, 2000). Additional information about the sorted cells can be obtained including, for example, the antibody-binding capacity, which is an index of the absolute number of surface receptors present on the target cells (Vogt et al., 2000).

Cell Transplantation Therapies

The cells of the present invention are useful for the treatment of any disorder of the central nervous system that is characterized by neural cell loss and/or would benefit from neural cell replacement therapy. Disorders of the nervous system amenable to treatment include, for example, traumatic brain and spinal cord injuries and neurodegenerative diseases including, without limitation, Parkinson's disease, Alzheimer's disease, Huntington's disease, stroke, amyotropic lateral sclerosis, spinocerebellar degenerations, such as spinal ataxia, Friedreich's ataxia, cerebellar cortical degenerations, and the like. Treatment of multiple sclerosis and other demyelinating diseases may also be possible using homogenous cell populations of this invention.

Cell transplantation therapies typically involve the intra-parenchymal (e.g., intracerebral) grafting of the replacement cell populations into the lesioned region of the nervous system, or at a site adjacent to the site of injury. Most commonly, the therapeutic cells are delivered to a specific site by stereotaxic injection. Conventional techniques for grafting are described, for example, in Bjorklund et al. (Neural Grafting in the Mammalian CNS, eds. Elsevier, pp 169-178, 1985), Leksell et al. (Acta Neurochir., 52:1-7, 1980) and Leksell et al. (J. Neurosurg., 66:626-629, 1987). Identification and localization of the injection target regions will generally be done using a non-invasive brain imaging technique (e.g., MRI) prior to implantation (see, for example, Leksell et al., J. Neurol. Neurosurg. Psychiatry, 48:14-18, 1985).

Briefly, administration of cells into selected regions of a patient's brain may be made by drilling a hole and piercing the dura to permit the needle of a microsyringe to be inserted. Alternatively, the cells can be injected into the brain ventricles or intrathecally into a spinal cord region. The cell preparation of the invention permits grafting of the cells to any predetermined site in the brain or spinal cord. It also is possible to effect multiple grafting concurrently, at several sites, using the same cell suspension, as well as mixtures of cells.

Following in vitro cell culture and isolation as described herein, the cells are prepared for implantation. The cells are suspended in a physiologically compatible carrier, such as cell culture medium (e.g., Eagle's minimal essential media), phosphate buffered saline, Hanks balanced salt solution, or artificial cerebrospinal fluid (aCSF). Cell density is generally about $10^4$ to about $10^7$ cells/µl, and preferably about 25,000 to about 100,000 cells/µl. The volume of cell suspension to be implanted will vary depending on the site of implantation, treatment goal, and cell density in the solution. For example, for treatments in which cells are implanted into the brain parenchyma (e.g., in the treatment of Parkinson's Disease), about 5-60 µl of cell suspension will be administered in each injection. Several injections may be used in each host, particularly if the lesioned brain region is large. Alternatively, administration via intraventricular injection, for example, will accommodate relatively larger volumes and larger cell numbers (see, for example, Madrazo et al., New Engl. J. Med., 316:831-834, 1987; Penn et al., Neurosurgery, 22:999-1004, 1988).

In some embodiments, the cells are encapsulated within permeable membranes prior to implantation. Encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. Several methods of cell encapsulation are well known in the art, such as described in European Patent Publication No. 301,777, or U.S. Pat. Nos. 4,353,888, 4,744,933, 4,749,620, 4,814,274, 5,084,350, and 5,089,272.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquified using sodium citrate. This creates a single membrane around the cells that is highly permeable to relatively large molecules (MW~200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off~40-80 kDa).

Example 1

Human Embryonic Stem Cell Culture and Differentiation

Human ES cell lines H1 (WA-01, XY), H7 (WA-07, XX), and H9 (WA-09, XX) were propagated according to previously published methods (Sonntag et al., Stem Cells, 25: 411-418, 2007). Briefly, hESCs were propagated on Mitomycin-C-treated human fibrobasts (D551, ATCC) in serum replacement medium (SRM; Dulbecco's modified Eagle's medium with 10% fetal bovine serum. Neuroectodermal differentiation of hESCs, to produce multipotent neural cells, was induced by coculture on transgenic MS5-Wnt1 stromal feeder cells. The hESCs were then triturated and plated at a density of about 0.5-1.0 colonies per six-well plate on a confluent layer of mitotically inactivated MS5-Wnt1 cells using SRM for 14 days, followed by N2 medium (DMEM/F-12; Invitrogen Corp). Neuroectodermal induction was achieved with and without the addition of 300 ng/ml Noggin (R&D Systems, Inc.) administration for 21 days. As shown in FIG. 1, hESCs progressively adopt a neuronal phenotype in culture. Multipotent neural cell induction was characterized by the formation of rosettes at DIV 21 and the accumulation of cells with an increasingly neuronal phenotype through DIV 42. These differentiated hESCs (mixed multipotent neural cells) were the subject of further experimentation.

Figure 2B:
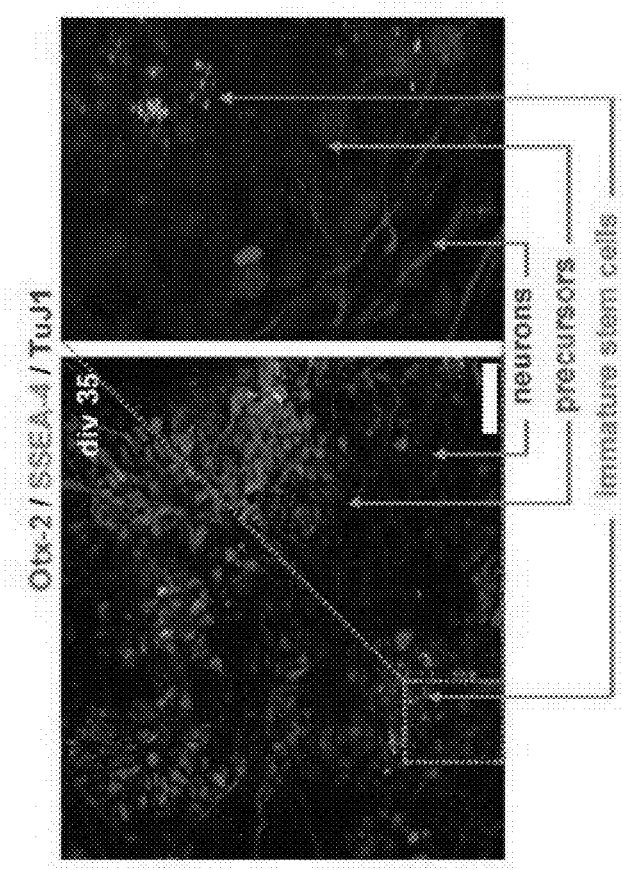
FIG. 2B is a series of photomicrographs of the differentiated hESCs following fluorescence immunocytochemistry for Otx-2, SSEA-4, and TuJ1. This figure demonstrates that the neuronal differentiation protocol results in mixed cultures, at DIV 35, which contain relatively mature neurons, neuronal precursors, and immature stem cells.
Figure 2A:
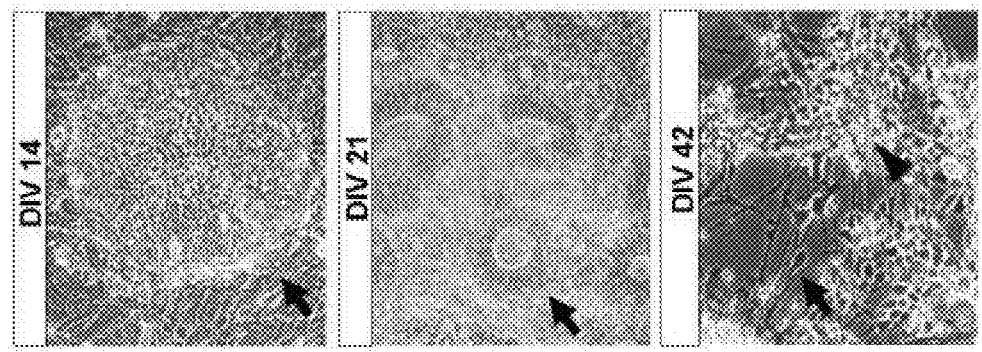
FIG. 2A is a series of photomicrographs showing the morphological changes associated with hESC differentiation according to the culture protocol described herein.

The neural cells at DIV 21 were further differentiated along a dopaminergic pathway using a combination of additional growth factors. A dopaminergic phenotype was induced by maintaining the neural stem cell rosettes in the presence of the following growth factor combination: 200 ng/ml sonic hedgehog (SHH), 100 ng/ml fibroblast growth factor 8 (FGF8), 20 ng/ml brain-derived neurotrophic factor (BDNF), 20 ng/ml basic fibroblast growth factor (bFGF), 1 ng/ml transforming growth factor type beta-3 (TGF-β3), 10 ng/ml glial cell line-derived neurotrophic factor (GDNF), 0.5 mM dibutyryl cAMP, and 0.2 mM ascorbic acid (AA). After 9 days (DIV 30) of this additional growth factor exposure, cells were passaged and resuspended in N2 medium, plated (50,000-100,000 cells/cm$^2$) in the absence of bFGF, but in the presence of BDNF, AA, SHH, and FGF8. After an additional 7 days of culture (DIV 37), cells were differentiated until DIV 42 or DIV 49 in the absence of SHH and FGF8 but in the presence of BDNF, AA, cAMP, GDNF, and TGF-β3 (see, FIG. 1). This differentiation protocol resulted in mixed cultures of continuously proliferative neural precursor cells (Otx2$^+$), differentiated neuronal cells (TuJ1$^+$), and clusters of immature SSEA-4$^+$ stem cells (FIGS. 2A-2B).

The cellular heterogeneity was not eliminated by prolonged culture times. Even at later stages of hESC differentiation, clusters of differentiated neuronal subtypes coexist with comparably more immature Nestin$^+$ proliferative cells and also non-neural cell types. These findings suggest that the presence of a proliferative pluripotent population at a given time point leads to heterogeneity of cell fate and of developmental stage (anisochronicity), which may compromise and transplantation therapies.

Example 2

Isolation and Characterization of Multipotent Neural Cell Populations Using FACS Fetal neural tissue has been dissociated and successfully used as cell suspensions in clinical trials of neural cell therapy (e.g., Mendez et al., Brain, 128: 1498-1510, 2005). This proves that certain post-mitotic neuronal cells can be harvested, resulting in a round-shaped cells, and subsequently regain neuronal morphology and functionality after in vitro culture and/or implantation into the brain. The following experiment demonstrates a FACS procedure that may be used to purify particular neuronal cell types for further in vitro and therapeutic uses.

The neural cells produced in Example 1 (DIV 42) were suspended as single cells and subjected to "gentle" fluorescence-activated cell sorting (FACS). The gentle FACS procedure has been previously optimized for process-bearing cells on variable including osmolality, nozzle size, and sheath pressure (Pruszak et al., Stem Cells 25: 2257-2268, 2007). Briefly, cells were harvested by mechanical selection or 0.05% Trypsin/EDTA or TrypLE Express (Gibco). Gentle trituration was used, and cells were filtered through cell strainer caps (35 µm mesh) to obtain a single cell suspension (about $10^6$ cells/ml for analysis and about $0.5-2.0\times10^7$ cells/ml for FACS). Surface antigens were labeled by incubating the cells with the appropriate primary antibodies for 30 minutes in the dark at 4° C., to prevent antibody internalization, and then for 20-30 minutes with the appropriate Alexafluor-488 or Alexafluor-647 fluorescent secondary antibodies. All washing steps were performed in phenol-free, $Ca^{2+}$-free, $Mg^{2+}$-free Hank's buffered saline solution (Gibco) containing penicillin-streptomycin, 20 mM D-glucose, and 2% fetal bovine serum). The stained cells were analyzed and sorted on a fluorescence-activated cell sorter FACSAria (BD Biosciences) using FACSDiva software. Data were additionally analyzed using FlowJo software (Tree Star). The fluorochromes were excited with the instrument's standard 488 nm and 633 nm lasers, and green fluorescence was detected using 490 LP and 510.20 filters and far red fluorescence using 660/20 filters. All analyses and sorts were repeated at least three times, and purity of sorted fractions was checked visually and by FACS reanalysis. A 100 µm ceramic nozzle (BD Biosciences), sheath pressure of 20-25 psi, and an acquisition rate of 1,000-3,000 events per second were used as conditions optimized for neuronal cell sorting. Parallel cultures were also sorted using a standard FACS methodology (70 psi, 70 µm nozzle) and an immunomagnetic cell separation procedure, for comparison purposes (Pruszak et al., 2007).

Figure 3A:
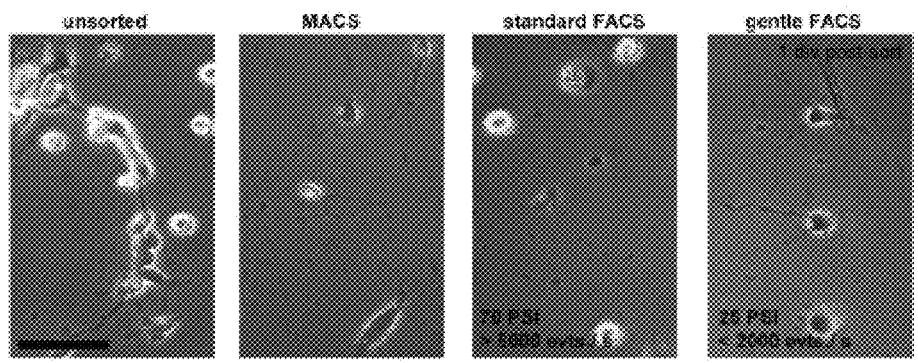
FIG. 3A is a series of photomicrographs showing the morphology of neural cells following dissociation ("unsorted"), MACS, standard FACS (70 psi nozzle pressure and 70 μm nozzle), and the modified "gentle" FACS (25 psi nozzle pressure and 100 μm nozzle) (scale bar: ~100 μm).
Figure 3B:
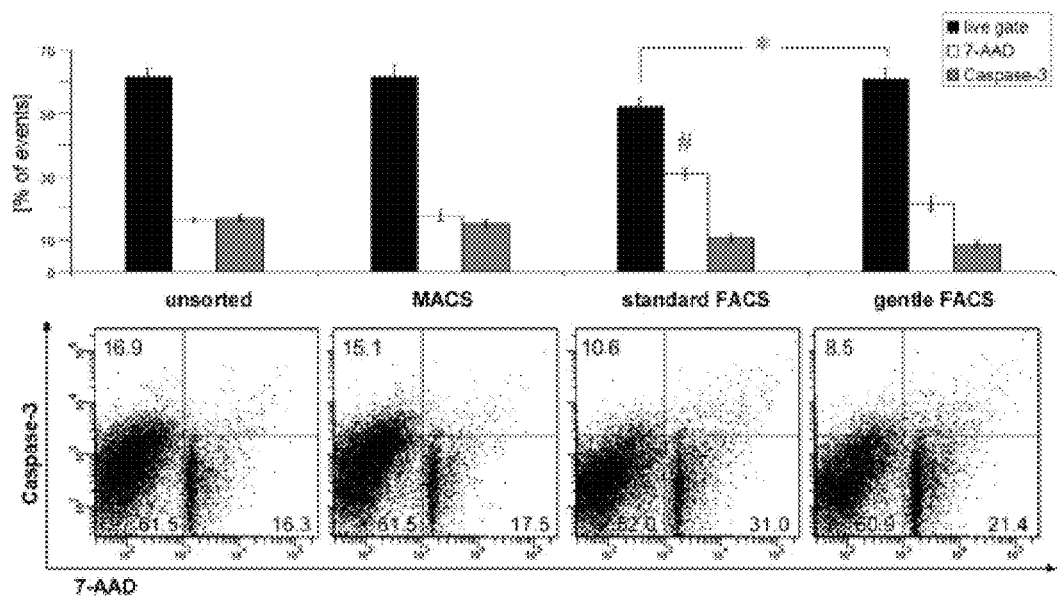
FIG. 3B shows the results of capase-3 (early apoptotic marker) and 7-AAD (marker of cell membrane permeability) FACS sorting following the cell sorting techniques described for FIG. 3A. The level of 7-AAD permeability was significantly increased (#: $p<0.05$) relative to the other sorting techniques (*: $p<0.05$).
Figure 3C:
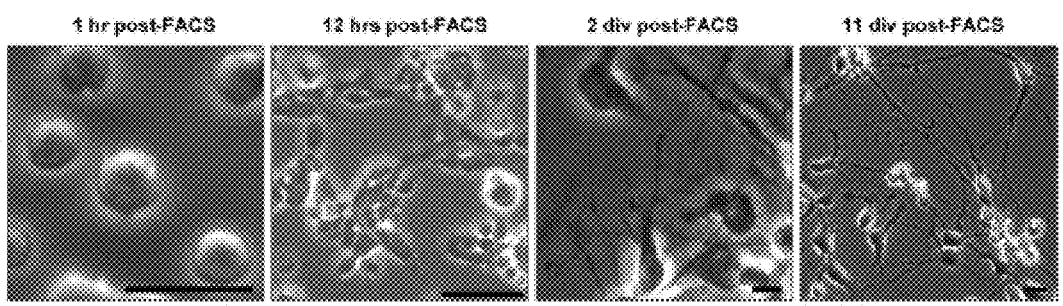
FIG. 3C is a series of photomicrographs showing the morphology of neural stem cells cultured following the cell sorting using the gentle FACS methodology (scale bar: 50 μm).

A comparison of cell selection methodologies (FIGS. 3A-3B) showed that cells isolated using gentle FACS were comparable to unsorted controls and cells selected by immunomagnetic cell section, with regard to cell viability as determined by caspase-3 activation and 7-AAD (7-aminoactinomycin D) nuclear dye uptake. Gentle FACS was superior to the standard FACS procedure. Replating of the gentle FACS-sorted cells resulted in cellular attachment within 1-2 hours, process re-extension within 12 hours, and the elaboration of an extensive neuronal network after two days (FIG. 3C).

Example 3

HESC Surface Marker Expression During Neuronal Differentiation

Figure 4:
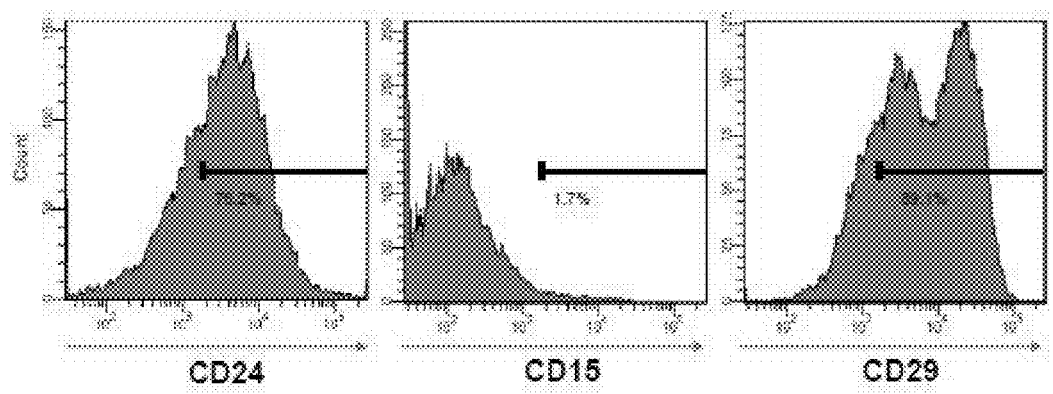
FIG. 4 shows the results of single-parameter FACS using neural stem cells cultured in vitro from hESCs.

Single-parameter flow cytometric analysis of mixed neural cultures (Example 1; DIV 30-40) was performed using the gentle FACS procedure described in Example 2. As shown in FIG. 4, CD24 and CD29 were present on major fractions of the cultured cells, while CD $15^+$-positive cells comprised only a minor subset of the total cell population.

Example 4

Selection for CD24 Reduces Proliferative Cell Types and Enriches Neuronal Cell Types The CD24 cell population isolated in Example 3 was further subdivided into $CD24^{HI}$ and $CD24^{LO}$ groups based on FACS signal intensity. The CD24 sorting criterion (fluorescence cut-off value) is showing in FIG. 4. About 76% of sorted cells were identified as $CD24^{HI}$. Each cell population was replated for further study.

Figure 5A:
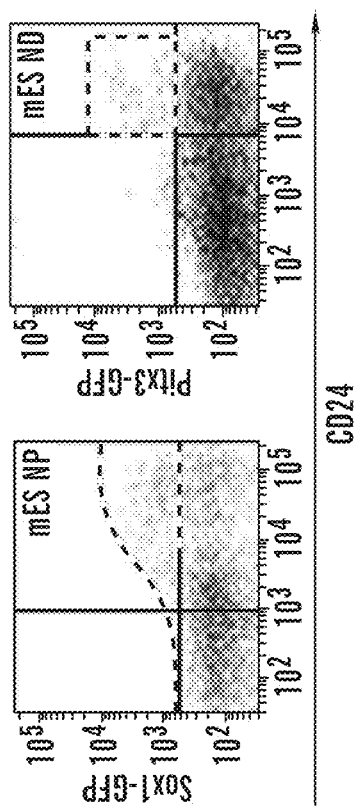
FIG. 5A shows the results of FACS sorting for CD24 and either Sox1-GFP or Pitx3-GFP, demonstrating the presence of mature neurons in $CD24^{HI}$ subpopulations of cultured ES cells.

A murine ES cell line containing a Sox1-GFP reporter (Chung et al., J. Neurochem. 97: 1467-1480, 2006) was used to investigate neural differentiation. At early stages of differentiation (DIV 14), CD24 expression correlated with neural phenotype induction (FIG. 5A, left panel). At later stages of neural differentiation in vitro, transgenic mouse ES cell-derived Pitx3-GFP+ dopamine neurons served as an indicator of CD24 expression on differentiated mature neuronal cells (FIG. 5A, right panel).

Figure 5B:
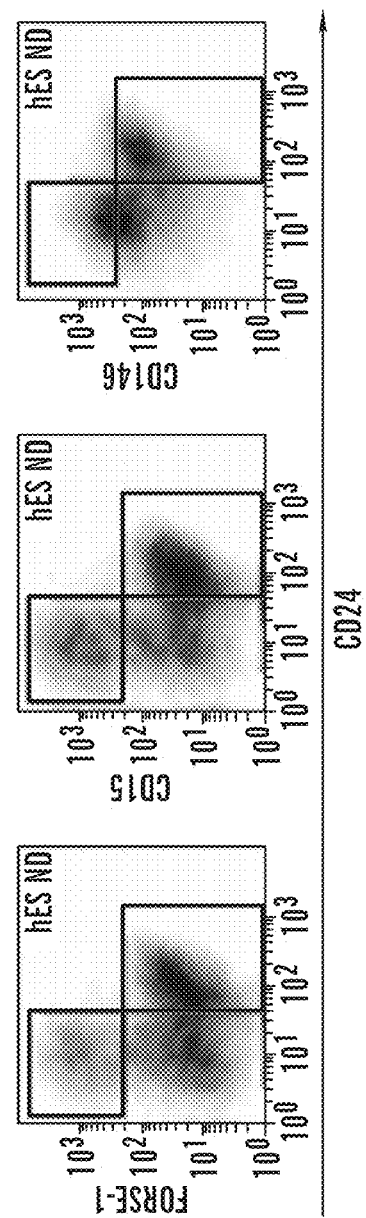
FIG. 5B shows the results of FACS sorting on the $CD24^{HI}$ population for the neural precursor and/or stem cell markers FORSE1, CD15, and CD146.

Bivariate FACS analysis identified that $CD24^{HI}$ cells were negative for early neural markers such as the FORSE1, CD15, and CD146 antigens (FIG. 5B). Additionally, $CD24^{HI}$ cells were negative for CD133 (Prominin-1; data not shown). CD133-positive cells are a subset of the CD15+ population (data not shown).

Figure 5C:
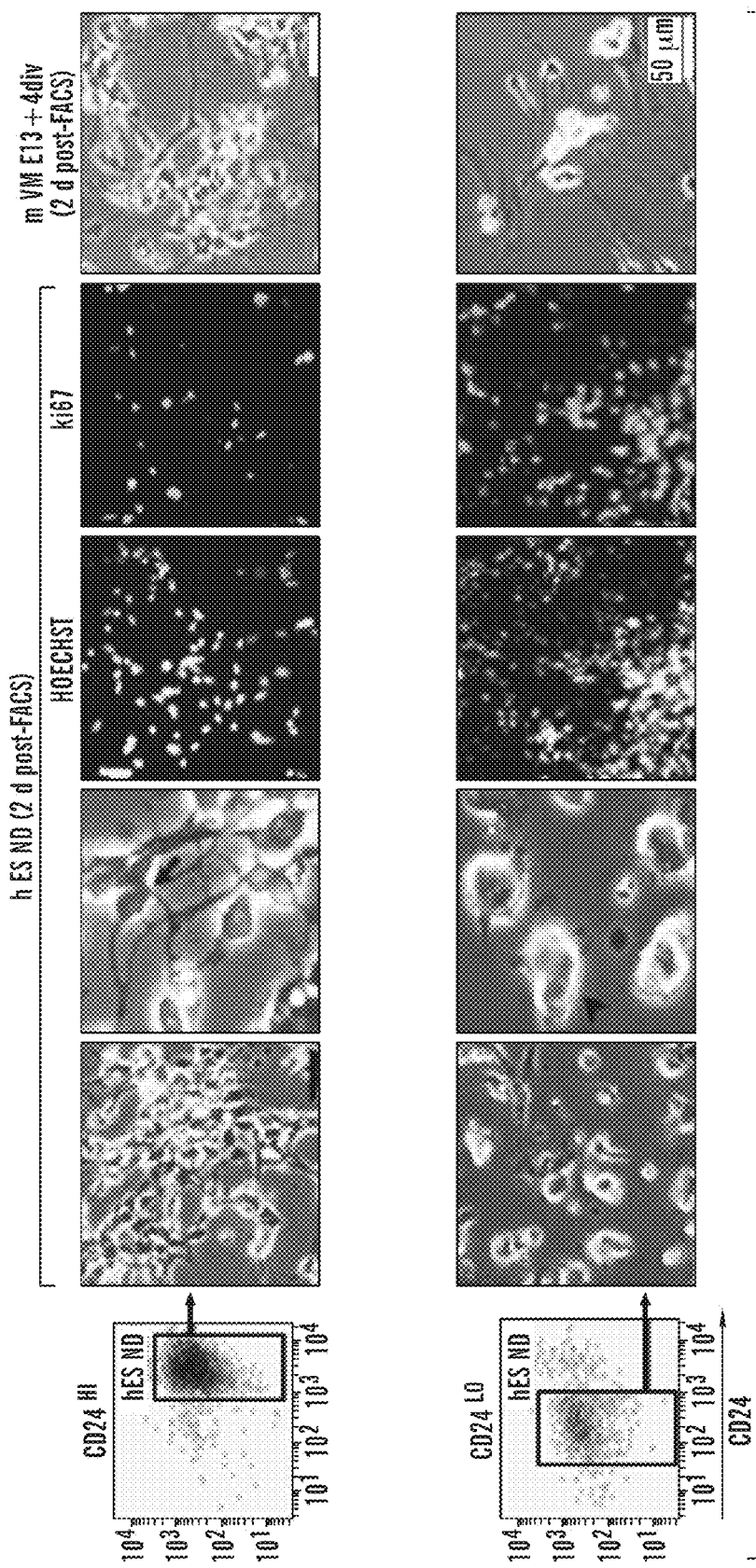
FIG. 5C is a series of photomicrographs showing cultured $CD24^{HI}$ (top row) and $CD24^{LO}$ (bottom row) cells (DIV 40-45). $CD24^{HI}$ cells displayed lower cell numbers (Hoechst) and were less proliferative (ki67) than $CD24^{LO}$ cells.

Cell sorting of human ES cell-derived neural cell suspensions facilitated the prospective enrichment of $CD24^{HI}$ and $CD24^{LO}$ subpopulations (FIG. 5C). Post-FACS cell cultures of the $CD24^{HI}$ population were highly enriched for neurons and displayed significantly less proliferative ki67+ cells compared to the $CD24^{LO}$ fraction. Consistent with these finding, the neuronal fraction of primary mouse brain cell preparations (embryonic day 13; "mVM E13") was enriched by selecting for $CD24^{HI}$ expression (FIG. 5C). $CD24^{HI}$ cultures displayed extension of neuronal processes forming a dense network immunoreactive for neuronal markers such as Tuj1, MAP2, and Synapsin (FIG. 5D-5E).

Figure 5F:
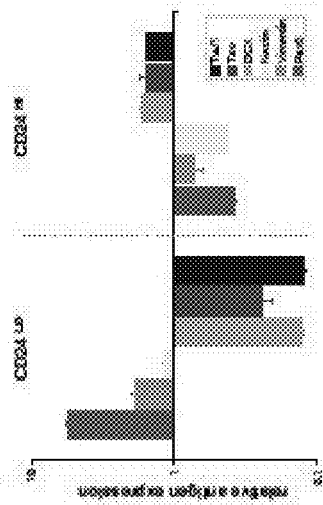
FIG. 5F is a bar graph showing the relative expression of a variety of markers in $CD24^{HI}$ and $CD24^{LO}$ cells.
Figure 5E:
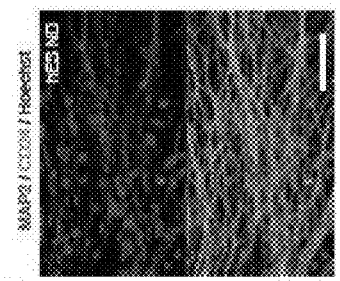
FIG. 5D-5E are photomicrographs showing that cultured $CD24^{HI}$ cells formed networks of neuronal processes stained with neuronal markers including TuJ1 (beta-III tubulin) and MAP2.
Figure 5D:
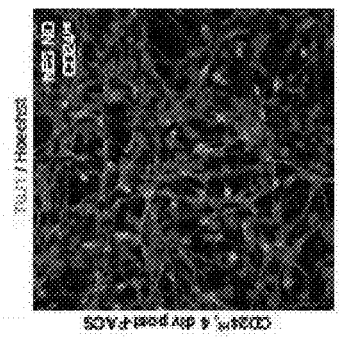

Overall, the $CD24^{LO}$ fraction was defined as consisting primarily of an immature neural phenotype, expressing markers such as Pax6, Vimentin and Nestin (FIG. 5F, left panel), while the $CD24^{HI}$ cells were strongly positive for neuroblast (doublecortin) and neuronal markers (TuJ1, Tau) (FIG. 5F, right panel). Taken together, these data, along with the other data provided herein, demonstrate that the $CD24^{LO}$ fraction of mixed multipotent neural cell cultures are immature and contribute to the tumorigenic potential of pluripotent cell transplantation therapies; whereas the $CD24^{HI}$ fraction contains more mature neuronal phenotypes and confers therapeutic benefit.

Example 5

CD15 is Expressed on Immature Neuroepithelial Cells

Figure 9A:
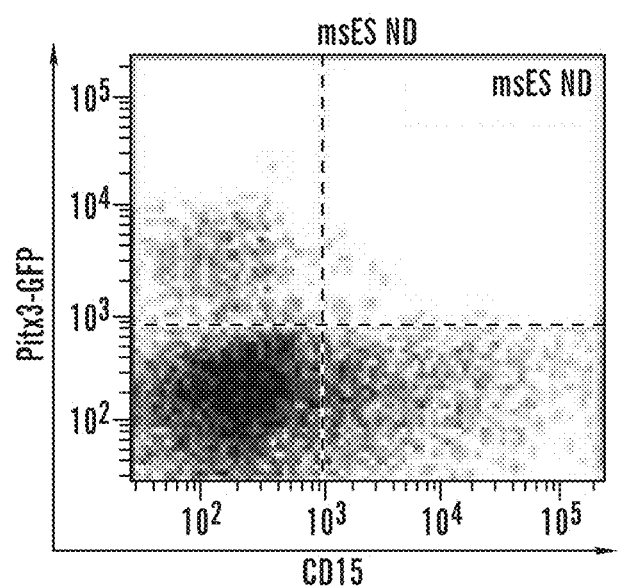
FIG. 9A shows that CD15 expression is absent in the early neurons/neuroblast subpopulation identified as Pitx3-GFP-positive.

The murine ES cell line containing a Sox1-GFP reporter described in Example 4 (Chung et al., J. Neurochem. 97: 1467-1480, 2006) was sorted based on CD15 (murine SSEA-1, human SSEA-3, Lewis-X antigen) expression. CD15, known to be a marker of immature cells, was absent on differentiated neurons, for example dopamine neurons identified by Pitx3-GFP expression (FIG. 9A). Consistent with its presence in immature neurons, CD15 was expressed by E13 mouse neuroepithelial cells (FIG. 9B; midbrain sections). CD15 was strongly expressed on Sox1 and Sox2-positive neuroepithelial rosette structures in cultured human ES cells (FIG. 9C). Such clusters are typical for the neural induction stage of human ES cell differentiation, but were also found at the differentiated stage due to incomplete patterning of such artificial developmental systems, contributing to the cellular heterogeneity and tumor-forming potential of human ES cell-derived neural cultures. CD15 expression may be used as a marker for selecting (or alternatively: eliminating) immature, neuroepithelial cells in developmental as well as transplantation paradigms.

Example 6

CD29 is Highly Expressed on Proliferative Cells

The murine ES cell line containing a Sox1-GFP reporter described in Example 4 (Chung et al., J. Neurochem. 97: 1467-1480, 2006) was sorted based on the CD29 surface antigen (beta1-integrin). CD29 was found to predominantly label the typical neuroepithelial rosette structures (FIG. 9D). While doublecortin-positive neuroblasts emerging from those more immature clusters were negative for CD15 and also CD29 expression, a second population of "flat" proliferative cells, typically forming a halo around dense neuroepithelial cell groups, was identified to strongly express CD29 (FIG. 9D). FACS analysis and cell sorting demonstrated that the $CD29^{HI}$ fraction was enriched for proliferative spherical clusters as well as proliferative adherent cell types (FIG. 9E). The $CD29^{LO}$ fraction was highly enriched for process-bearing post-mitotic neurons (FIG. 9E).

Example 7

Combinatorial Analysis of CD15 and CD29 Define Distinct Subpopulations

Figure 6:
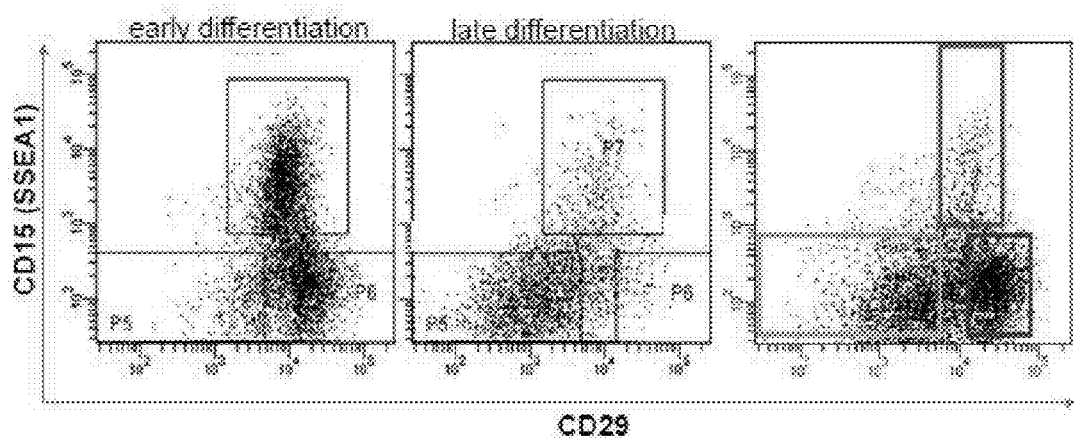
FIG. 6 shows the results from bivariate FACS analysis of CD15 and CD29 for early and late differentiation neural cell populations. The sorted cells were characterized as indicated by the boxed regions, wherein the $CD29^{MID/LO}/CD15^-$ cells were captured from the group indicated by the box in the lower left corner, $CD29^{MID/HI}/CD15^-$ cells were captured from the group indicated by the box in the lower right corner, and $CD29^{MID/HI}/CD15^+$ cells were captured from the group indicated by the box in the upper middle of the panels.

The neural cell populations of Example 1 were subjected to gentle FACS with bivariate sorting based on the level of CD15 and CD29 expression. Consistent with the results shown in FIG. 4, cells were essentially either CD15$^+$ or CD15$^-$. The CD15 sorting criterion (fluorescence cut-off value) is showing in FIG. 4, in which about 1.7% of sorted cells were identified as CD15$^+$. Cell were sorted into three sub-groups based on CD29 expression levels: $CD29^{HI}$, $CD29^{MID/HI}$, and $CD29^{MID/LO}$. As shown in FIG. 6, the CD15$^+$ cells represented subsets of the $CD29^{MID/HI}$ population which was more prominent at early neural differentiation stages (FIG. 6, left panel), and decreased over time in culture (FIG. 6, middle panel). As summary of the three subpopulations is shown in the right panel of FIG. 6, wherein the $CD29^{MID/LO}$/CD15$^-$ cells were captured from the group indicated by the box in the lower left corner, $CD29^{HI}$/CD15$^-$ cells were captured from the group indicated by the box in the lower right corner, and $CD29^{MID/HI}$/CD15$^+$ cells were captured from the group indicated by the box in the upper middle of the panel.

Example 8

Figure 7A:
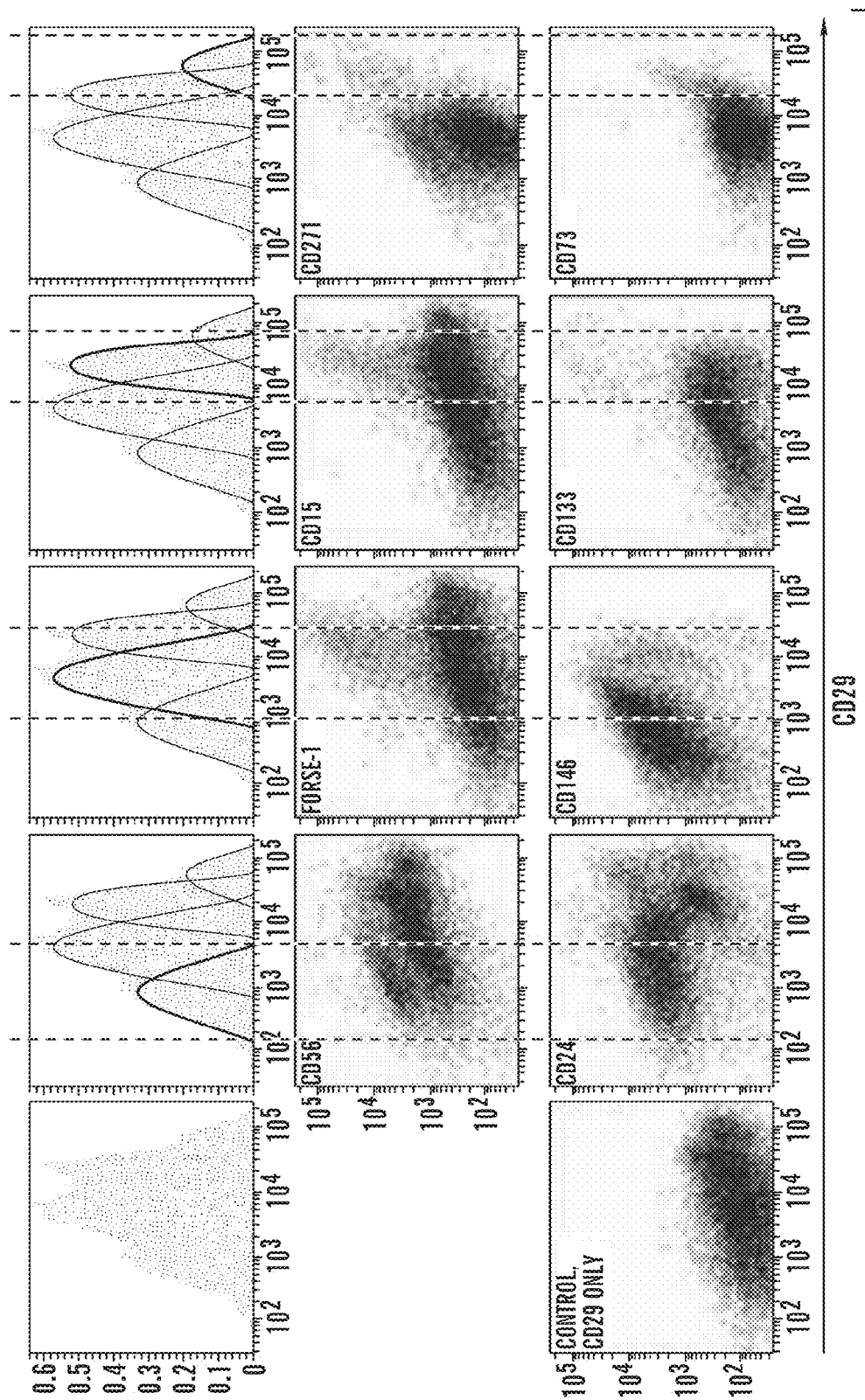
FIG. 7A shows the results of combinatorial FACS analysis of CD15, CD24, and CD29 with various additional markers that further characterize the specific neural cell subpopulations. The shaded areas and dashed lines represent the cell sorting criteria for the various subpopulations.
Figure 7B:
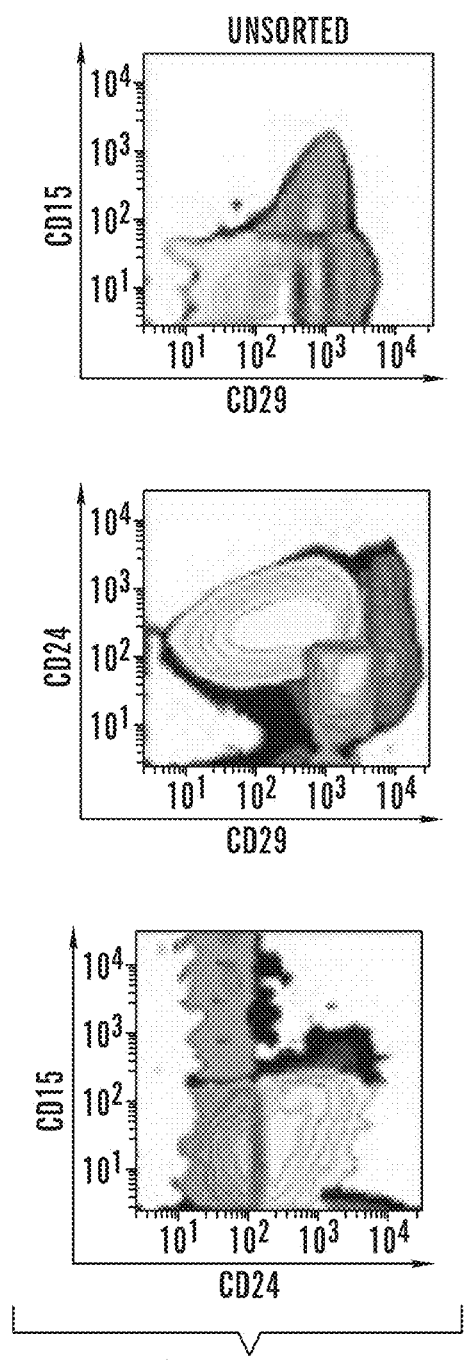
FIG. 7B shows the results of FACS analysis in each of the pairwise combinations when cells were sorted for CD15, CD24, and CD29.
Figure 7C:
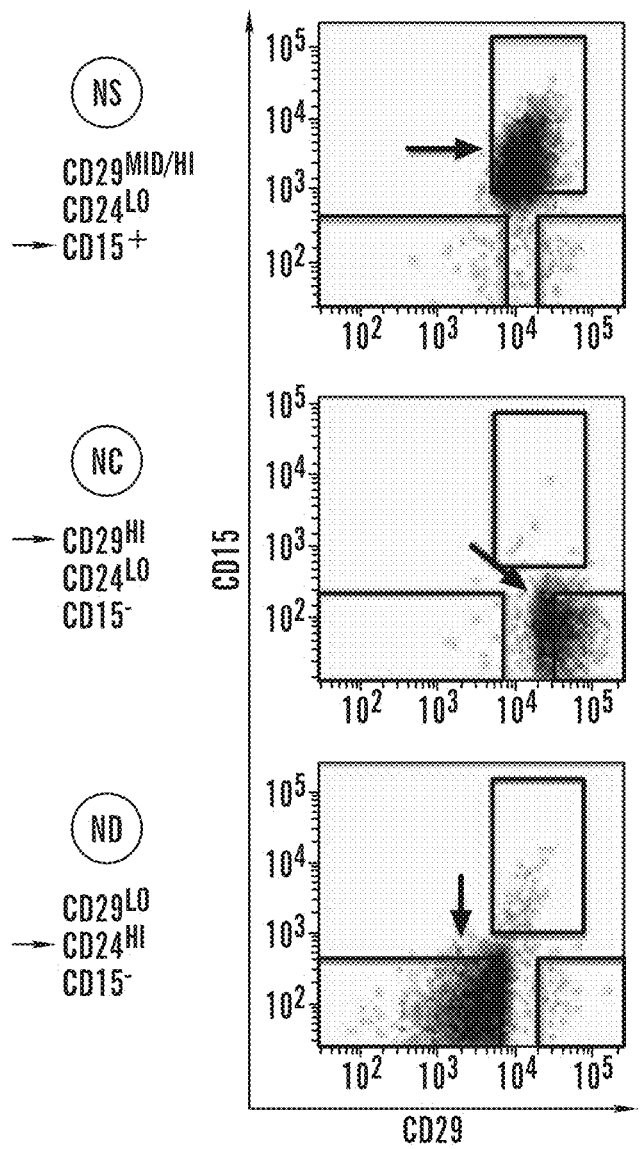
FIG. 7C identifies the marker combination for each of the three subpopulations, and their location relative to the FACS results shown in FIG. 7B.

Multiple Neural Cell Subpopulations Identified by Multivariate Surface Antigen Analysis The neural cell populations of Example 1 were subjected to multivariate FACS analysis based on their expression of CD15, CD24, and CD29, along with various addition markers. FIG. 7A shows the surface antigen profiles of $CD29^{LO}$ (second column), $CD29^{LO/MID}$ (third column), $CD29^{MID/HI}$ (fourth column), and $CD29^{HI}$ (fifth column) neural cells in conjunction with a variety of other cell surface markers. FIGS. 7B-7C show the existence of several distinct cell populations identified by FACS, including population a population of neural precursor cells ("NS") which is CD15$^+$/$CD24^{LO}$/$CD29^{MID/HI}$; a population of neural crest/mesenchymal cells ("NC") which is CD15$^-$/$CD24^{LO}$/$CD29^{HI}$, and a population of early neurons/neuroblasts ("ND") which is CD15$^-$/$CD24^{HI}$/$CD29^{LO}$. When applying these surface antigens in combination, distinct cell populations were isolated that were >80% specific for the desired cellular subsets (FIG. 7C).

Figure 7D:
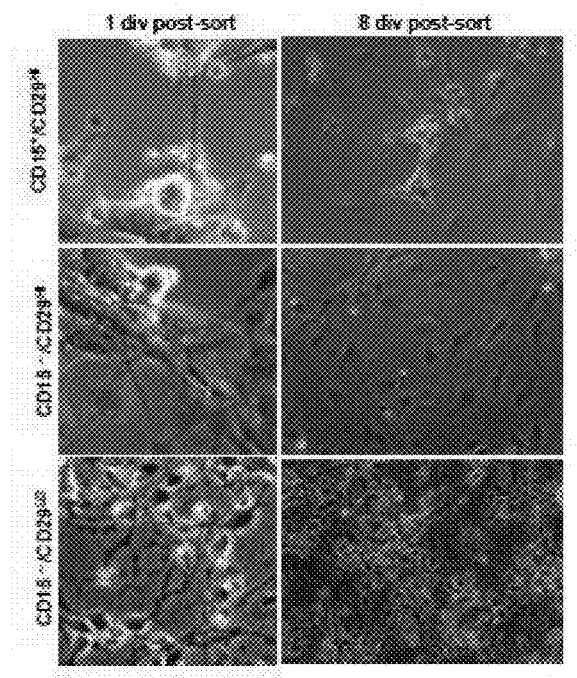
FIG. 7D shows each of the three subpopulations in culture at DIV 1 and DIV 8 after sorting.

Each of the three subpopulations was cultured and examined by confocal microscopy (FIG. 7D). The neural precursors cells ("NS") were enriched for proliferative clusters, including neurospheres. Secondary neurospheres could be efficiently derived from this population. The neural crest cells ("NC") presented with massive proliferation of flat, adherent cells after cell sorting. In contrast, the early neurons/neuroblast subset ("ND") displayed a highly enriched neuronal cell culture.

Example 9

Analysis of Neural Cell Subpopulations

Figure 8A:
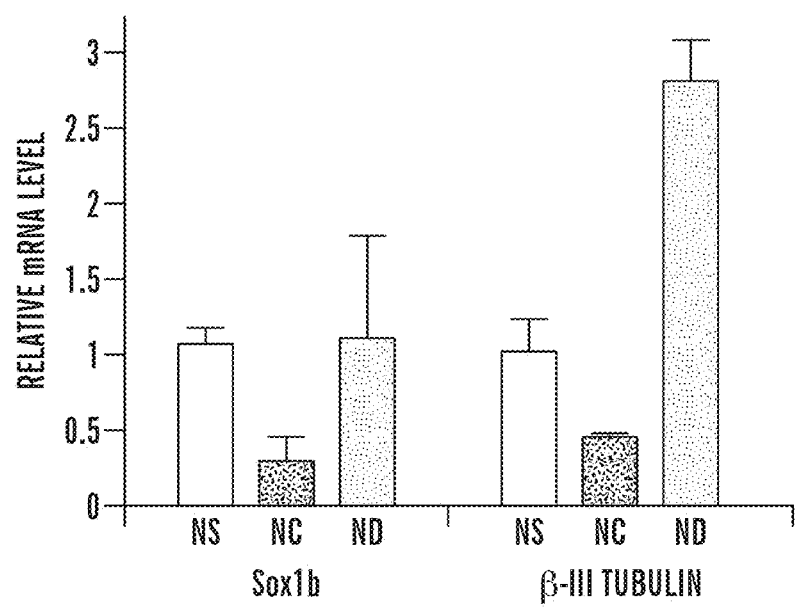
FIG. 8A shows the results of quantitative PCR for Sox1b and TuJ1 (betaIII-tubulin) in $CD29^{MID/HI}/CD15^+$ cells (left bars), $CD29^{HI}/CD15^-$ cells (middle bars), and $CD29^{MID/LO}/CD15^+$ cells (right bars).

The neural cell subpopulations produced in Example 8 were further characterized using FACS and immunocytochemistry. FIGS. 8A-8B show that the neuronal intracellular antigen TuJ1 (betaIII-tubulin) and Sox-1 are present in high levels in the CD15$^-$/$CD24^{HI}$/$CD29^{LO}$ cells, suggesting that this subpopulation contains a significant fraction of neurons or neuronal precursors, confirming the previous characterization that these cells are early neurons and/or neuroblasts and are more differentiated than the other two subpopulations. The CD15$^-$/$CD24^{HI}$/$CD29^{LO}$ subpopulation was cultured and exhibited almost exclusively neuronal morphology (FIG. 8C).

Example 10

In Vivo Transplantation of Neural Cell Subpopulations

In vivo transplantation experiments were performed in order to further delineate the biological properties of the various neural cell subpopulations. These experiments used female Sprague-Dawley rates (200-250 g) that received a unilateral striatial lesion using 6-hydroxydopamine (6-OHDA).

Following FACS purification, the neural cell subpopulations were resuspended at ~25,000 viable cells per microliter in the final differentiation medium. Four microliters of each cell suspension were slowly injected into the striatum of subject rats (anterior-posterior=0; lateral=−2.8 mm from bregma and −5.5 mm to −4.5 mm from ventral from dura, with the tooth bar set at −3.3; also see, Sonntag et al., Stem Cells 25: 411-418, 2007). Five weeks after transplantation, animals were terminally anesthetized, perfusion-fixed using paraformaldehyde. The brains were removed and post-fixed prior to processing for immunohistochemical analysis.

Human cells in the rodent brain were identified by immunohistochemical analysis using an antibodies against human nuclear antigen (HuN) (1:50; Chemicon), human NCAM (Eric-1; Santa Cruz), and TH (1:250; Pel-Freez). Primary antibodies were visualized using appropriate fluorescently-labeled secondary antibodies and confocal microscopy. Nuclei were visualized using Hoechst 33342 (5 µg/ml). In order to identify signal co-localization within a cell, optical sections were kept to a minimal thickness and orthogonal reconstructions were analyzed.

FIGS. 8D-8E demonstrate that each of the three subpopulations generated stable and defined neural grafts in lesioned striata. The CD15$^+$/$CD24^{LO}$/$CD29^{HI}$ (neural precursor) grafts contained proliferative neuroepithelial "rosette-like" cells, confirming the in vitro characterizing of this subpopulation of neural stem cells. These rosettes are characteristic of neuroepithelial tumors and the cells further were immunoreactive for Sox2, Nestin, and radial glial markers (3CD2 and RC2). Grafts of the neural crest/mesenchymal cell subpopulation (CD15$^-$/CD24$^{LO}$/CD29$^{HI}$) showed similar evidence of tumor formation. These grafts were also strongly positive for CD271, confirming that the transplanted cells retained their neural crest/mesenchymal phenotype.

By contrast, the early neuron/neuroblast (CD15$^-$/CD24$^{HI}$/CD29$^{LO}$) grafts were composed of hNCAM-positive cells that extended neuronal processes into the host tissue (FIG. 8F). No tumor formation was observed 4 weeks or 8 weeks after transplantation; compared to evidence of tumor formation as early as four weeks after transplantation of the other subpopulations. These morphological and immunohistochemical observations are confirmed by the relatively small graft size associated with the early neuron/neuroblast cells ("ND") versus grafts of the other cell types (FIG. 8G). Likewise, the early neuron/neuroblast grafts contained few, if any, ki67-positive cells relative to the other grafts (FIG. 8H). Thus, the CD15$^-$/CD24$^{HI}$/CD29$^{LO}$ grafts represent low- or non-proliferative neural compositions and are suitable for long-term transplantation.

Summary of Results

Mixed cultures of multipotent neural cells can be derived from hESCs and other pluripotent cell types, when maintained and differentiated under defined conditions. However, cell culture techniques alone cannot yield a homogenous and synchronized population of one particular cell type. The results of the foregoing experiments demonstrate that a modified FACS procedure (gentle FACS) may be used to isolate several neural stem cell subpopulations having defined characteristics, while maintaining the viability of those cells.

Several specific neural cell populations were identified and characterized based on three significant cell surface markers: CD15, CD24, and CD29. Neurons (e.g., early neurons and/or neuroblasts) express high level of CD24 and a low level of CD29, while the more immature neural crest/mesenchymal cells and neural precursor cells express low levels of CD24 and high levels of CD29. Thus, these two markers may be used individually or in combination to separate the more mature neuronal cell types from the more immature neural precursor and neural crest/mesenchymal cells. CD15 expression was observed on only the most immature cultured cell type; the neural precursor cells. The neural crest/mesenchymal cells and the early neurons/neuroblasts were predominantly CD15-negative. Thus, CD15 is a useful marker for further separating the CD24$^{LO}$/CD29$^{HI}$ cells into their component populations of neural precursors and neural crest/mesenchymal cells. CD15 status is also useful as a secondary selection to further eliminate proliferative cell types from the early neuron/neuroblast populations.

Unless otherwise defined, all technical and scientific terms used herein have the same meaning as commonly understood by one of ordinary skill in the art to which this invention belongs.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for isolating early neurons and neuroblasts of human origin from in vitro culture comprising:
   (i) culturing human pluripotent neural cells in the presence of a growth factor combination comprising sonic hedgehog (SHH), fibroblast growth factor-8 (FGF-8), basic fibroblast growth factor (bFGF), and brain-derived neurotrophic factor (BDNF) that induces at least some of said pluripotent cells to increase expression of TuJ1 relative to pluripotent cells cultured in the absence of said growth factor combination;
   (ii) further culturing the cells cultured under the growth factor combination under a second growth factor combination comprising SHH, FGF-8, and BDNF and not bFGF; and
   (iii) selecting the cells obtained from step (i) that express high levels of CD24, wherein said subpopulation is identified as early neurons and neuroblasts.

2. The method of claim 1 further comprising a step of removing CD15$^+$ cells from said subpopulation by subjecting the cells from said subpopulation to fluorescent assisted cell sorting (FACS).

3. The method of claim 2 further comprising a step of removing cells expressing high levels of CD29 by subjecting the cells from said subpopulation to fluorescent assisted cell sorting (FACS).

4. The method of claim 1, wherein the cells obtained in step (iii) represent not more 75% of the CD15$^-$ cells obtained from step (i).

5. The method of claim 1, wherein the cells obtained from step (iii) represent not more 25% of the CD15$^-$ cells from the cells obtained from step (i).

6. The method of claim 1, further comprising the step of culturing the cells culture under the second growth factor combination under a third growth factor combination consisting of FGF-8 and BDNF and not bFGF or SHH.

7. A method for isolating human neural crest cells from in vitro culture comprising:
   (i) culturing human pluripotent neural cells in the presence of a growth factor combination sonic hedgehog (SHH), fibroblast growth factor-8 (FGF-8), basic fibroblast growth factor (bFGF), and brain-derived neurotrophic factor (BDNF) that induces at least some of said pluripotent cells to increase expression of TuJ1 relative to pluripotent cells cultured in the absence of said growth factor combination;
   (ii) further culturing the cells cultured under the growth factor combination under a second growth factor combination comprising SHH, FGF-8, and BDNF and not bFGF;
   (iii) removing CD 15$^+$ cells from the cells obtained from step (ii) by fluorescent assisted cell sorting (FACS); and
   (iv) selecting cells that express relatively high levels of CD29 from the cells obtained from step (ii),
   wherein the cells obtained following steps (iii) and (iv) are identified as neural crest cells.

8. The method of claim 7, wherein the cells obtained from step (iv) represent not more than 75% of the CD15$^-$ cells obtained from step (i).

9. The method of claim 7, wherein the cells obtained from step (iv) represent not more than 25% of the CD15$^-$ cells obtained from step (i).

10. The method of claim 7, wherein said method further comprises selecting cells that express low levels of CD24.

11. A method for isolating human neural precursor cells from in vitro culture comprising:
- (i) culturing human pluripotent neural cells in the presence of a growth factor combination consisting of sonic hedgehog (SHH), fibroblast growth factor-8 (FGF-8), basic fibroblast growth factor (bFGF), and brain-derived neurotrophic factor (BDNF) that induces at least some of said pluripotent cells to increase expression of TuJ1 relative to pluripotent cells cultured in the absence of said growth factor combination;
- (ii) further culturing the cells cultured under the growth factor combination under a second growth factor combination comprising SHH, FGF-8, and BDNF and not bFGF,
- (iii) removing $CD15^-$ cells from obtained from step (ii); and
- (iv) selecting cells that express high levels of CD29 from the cells obtained from step (ii), wherein the cells obtained following steps (iii) and (iv) are identified as early neurons and neuroblasts.

12. The method of claim 11, wherein the cells obtained from step (iv) represent not more than 75% of the $CD15^+$ cells from said population cultured in step (i).

13. The method of claim 11, wherein the cells obtained from step (iv) represent not more than 25% of the $CD15^+$ cells from said population cultured in step (i).

14. The method of claim 11, wherein said method further comprises selecting cells that express low levels of CD24.

* * * * *